US006410795B1

(12) United States Patent
Fisch et al.

(10) Patent No.: US 6,410,795 B1
(45) Date of Patent: Jun. 25, 2002

(54) PROCESS FOR BASE-PROMOTED CONDENSATION REACTIONS AND BASE REAGENT THEREFOR

(75) Inventors: Michael H. Fisch, Wayne, NJ (US); Edward Krainer, Lynbrook, NY (US); Radu Bacaloglu, Hamburg, NJ (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 09/769,429

(22) Filed: Jan. 26, 2001

(51) Int. Cl.[7] .............................................. C07C 45/72
(52) U.S. Cl. ...................... 568/314; 568/315; 568/346; 568/347; 568/388; 568/391
(58) Field of Search ................................ 568/314, 315, 568/346, 347, 388, 391

(56) References Cited

U.S. PATENT DOCUMENTS

| | | |
|---|---|---|
| 3,001,970 A | 9/1961 | Mannheim-Fendenheim et al. .... 260/45.95 |
| 3,493,536 A | 2/1970 | Weisfeld et al. .......... 260/45.75 |
| 3,994,869 A | 11/1976 | Gontarz et al. ................. 526/1 |
| 4,427,816 A | 1/1984 | Aoki et al. .................. 524/357 |
| 4,482,745 A | 11/1984 | Maulding ................... 568/314 |
| 5,015,777 A | 5/1991 | Chisolm et al. ............. 568/314 |
| 5,344,992 A | 9/1994 | Drewes et al. ............... 568/314 |
| 5,672,646 A | 9/1997 | Allas et al. .................. 524/357 |
| 5,808,165 A | 9/1998 | Chassaing et al. ........... 568/314 |

FOREIGN PATENT DOCUMENTS

| | | |
|---|---|---|
| EP | 0 454 624 B1 | 10/1995 |
| EP | 0 507 013 B1 | 7/1996 |

OTHER PUBLICATIONS

Hauser et al., Organic Reactions, (vol. 8, 1959), Chapter 3, (pp. 59–197), The Acylation of Ketones to Form B–Diketones of B–Keto Aldehydes.
Magnani and McElvain in Organic Synthesis, Collective vol. 3, pp. 251–253. 1941.
Barnes et al., Journal of American Chemical Society, vol. 67, 1945, pp. 132–134, "A Study on the Direction of Enolization of p–Bromodibenzoylmethane."
Hausef et al., Journal of American Chemical Society, vol. 69, 1947, pp. 2649–2651, "The Claisen Benzoylation of Certain Methylene Ketones with Phenyl Benzoate by the Sodium Amide Method."
Wallet et al., Synthetic Communications, 26(22), 1996, pp. 4097–4103, "A Practical Synthesis of Dibenzoylmethanes."
Choshi et al., Chem. Pharm. Bull. 40(4), 1992, pp. 1047–1049, "Synthesis of Dibenzoylmethane Derivatives and Inhibition of Mutagenicity in Salmonella Typhimurium."
Suzuki et al., Journal of the American Chemical Society, 102:6, 1980, pp. 2095 and 2096, "Palladium (0) –Catalyzed Reaction of a, B–epoxy Ketones Leading to B–Diketones."
Katayama et al, Synthesis, 1988, pp. 178–183, "Synthesis of 1,3–Dicarbonyl Compounds by the Oxidation of 3–Hydroxycarbonyl Compounds with Corey–Kim Reagent."
Rao et al., J. Org. Chem., vol. 36, 1971, pp. 1447 and 1448, A New Synthesis of Symmetrical Diaroylmethanes.
Hill et al., Duke University, Dept. of Chemistry, vol. 81,pp. 602–606, 1958, "Rates of Condensation of Sodio Ketones with Esters to Form Sodio B–Diketones in Ether Solution."
Garrigues et al., Polymer Degradation and Stability 45 (1994) pp. 103–110, "Thermal Dehydrochlorination and Stabilization of poly(vinylchloride) in Solution."
Anselme, Organic Chemistry, 32(11), 1967, p. 3716, "A Convenient and Practical Preparation of Dibenzoylmethane."
Chemical Abstract, p. 85, 1974.

*Primary Examiner*—Sreeni Padmanabhan
*Assistant Examiner*—Sikarl A. Witherspoon
(74) *Attorney, Agent, or Firm*—Daniel Reitenbach; Paul Grandinetti

(57) ABSTRACT

A method for the preparation of 1,3-diketones is disclosed wherein the method comprises the steps of:

(A) mixing an alkali metal base with a hindered alcohol in an aromatic hydrocarbon solvent;

(B) boiling the mixture and azeotropically distilling water formed by the reaction between the base and the alcohol, whereby a solution of a hindered alkali metal alkoxide is formed in situ in the solvent;

(C) mixing an ester with the solution of the hindered alkali metal alkoxide in the aromatic hydrocarbon solvent; and then (D) adding a ketone to the mixture.

20 Claims, No Drawings

PROCESS FOR BASE-PROMOTED CONDENSATION REACTIONS AND BASE REAGENT THEREFOR

BACKGROUND OF THE INVENTION

1. Field of the Invention

This invention relates to a process for the preparation of beta-diketones and, more particularly, to a process for the production of beta-diketones by means of a homogeneous or nearly homogeneous liquid reaction medium wherein a carboxylic acid ester is reacted with a ketone in the presence of a condensing agent that is a sterically hindered alkali metal alkoxide dissolved in an aromatic hydrocarbon.

2. Description of Related Art

Beta-diketones are highly valuable compounds having advantageous utility in a wide variety of applications. For example, U.S. Pat. No. 3,001,970 discloses the use of dibenzoylmethane to prevent the discoloration of vinylidene chloride. U.S. Pat. No. 3,493,536 discloses that diaroylmethane compounds provide stabilizing action against the sensitizing effect of bismuth or antimony compounds on chlorine containing materials. Aryl substituted beta-diketones are shown by U.S. Pat. No. 3,994,869 to be useful as accelerators for the photodegradation of polyolefins. U.S. Pat. No. 4,427,816 discloses beta-diketones in combination with hydrotalcites as stabilizer compositions for halogen containing polymers.

The preparation of beta-ketones is reported in Organic Reactions (Vol. 8, 1959), Chapter 3, (pages 59–195) entitled "The Acylation of Ketones to Form β-Diketones or β-Keto Aldehydes." The article states in its introduction at page 61, "Under certain conditions, a ketone having an α-hydrogen atom may be acylated with an ester, an acid anhydride, or an acid chloride to form a β-diketone or, when the acylating agent is a formic ester, β-keto aldehyde. The process consists in the replacement of an α-hydrogen atom of the ketone by an acyl group; . . ."

Unfortunately, the acylation of ketones, as achieved by using previously known procedures, is a reaction that does not readily proceed in an economical manner. On page 66 of this same text, for example, it is pointed out that the acylation of ketones with esters in the presence of a basic reagent may be accompanied by certain side reactions. Among the side reactions that may occur are self-condensation of the ketone, self-condensation of the ester, aldol reaction of the ester with the carbonyl group of the ketone, or a Michael condensation of the ketone. Also, the basic condensing agent may react with the carbonyl group of the ester.

The preparation on a laboratory scale of dibenzoyl methane by the reaction of acetophenone and ethyl benzoate in the presence of sodium ethoxide and the absence of solvent is reported by Magnani and McElvain in Organic Synthesis, Collective Volume 3, pp. 251–253. This reaction used 4 moles of ethyl benzoate and 0.5 mole of acetophenone. The reaction mixture was gelatinous after all of the ethoxide had been added and was too viscous to be stirred with a Hershberg stirrer. The yield of dibenzoyl methane recovered from the reaction mixture, as reported, was 62–71% based on the acetophenone.

In general, the reaction of the ester, the ketone, and the basic condensing agent in the presence of an inert solvent is known, as in the aforementioned Organic Reactions article at page 112. This article further states that the beta-diketone may be isolated by the usual technique of distillation or filtration, but often it is isolated as its copper derivative from which the beta-diketones need to be regenerated by further chemical reactions with concomitant yield losses, generation of waste products, and laborious recovery of copper.

The use of copper derivatives is an expensive and environmentally undesirable procedure. Furthermore, the occurrence of side reactions would prevent the commercial success of the process. Then, too, loss of solvent and the need to use fresh solvent for each reaction is commercially unattractive.

U.S. Pat. No. 3,994,869, mentioned above, discloses the preparation of aryl substituted beta-diketones by the reaction of acetophenone or a substituted acetophenone with an ester in the presence of a base, such as sodium methoxide, sodium ethoxide, and sodium hydride. The acetophenone may be represented by the structural formula:

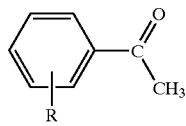

wherein R is selected from the group consisting of hydrogen, halogen, $C_1$ to $C_9$ alkyl and $C_1$ to $C_9$ alkoxy. Representative esters identified as useful in this reaction are methyl stearate, ethyl benzoate, ethyl acetate, and ethyl laurate. This reaction, according to the patent, can be carried out in a suitable aprotic solvent, such as toluene or tetrahydrofuran. Recovery of the desired product is stated to be by methods that are now known in the art.

While it has been known that beta-diketones can be made by the reaction of acetophenone or a substituted acetophenone with an ester in the presence of base, this procedure has drawbacks which have limited its commercial acceptability. U.S. Pat. No. 4,482,745 discloses that handling large quantities of strong bases, such as sodium ethoxide makes their use undesirable and costly for large scale production. Yet, sodium alkoxides are preferred bases since only one mole is consumed, whereas two moles of metallic sodium, sodium amide, or sodium hydride would normally be required. Then, too, metallic sodium or sodium hydride are more hazardous than the alkoxides. Aromatic beta-diketones in high yields and purity can be readily made by this process. The method taught by this patent comprises reacting acetophenone with from 5 to 10 molar equivalents of methyl benzoate in the presence of from 1 to 2 molar equivalents of calcium oxide, in a temperature range of from 150° to 200° C. for from three to six hours under an inert nitrogen atmosphere while continuously removing the methyl alcohol which is formed during the reaction.

U.S. Pat. No. 5,015,777 and European Patent No. 0 507 013 B1 disclose a process for the preparation of aromatic beta-diketones by the reaction of an acetophenone and a molar excess of an alphatic ester or an ester of benzoic acid in the presence of sodium alkoxide condensation agent in an aromatic hydrocarbon solvent. Also disclosed is a method of recycling the solvent and excess ester reactant after separation of the aromatic beta-diketone product.

U.S. Pat. No. 5,344,992 and European Patent No. 0 454 624 B1 disclose a process for the preparation of 1,3-diketones of formula I

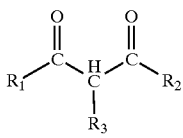
(I)

wherein $R_1$ and $R_2$ are each independently of the other $C_1$–$C_{20}$ alkyl, phenyl or phenyl which is substituted by halogen, hydroxy, $NO_2$, $C_1$–$C_4$ alkyl and/or $C_1$–$C_4$ alkoxy, $C_7$–$C_9$ phenylalkyl or a radical of formula II $$—A—X—R_4 \quad (II)$$

wherein A is $C_1$–$C_{12}$ alkylene, phenylene or phenylene which is substituted by halogen, hydroxy, $NO_2$, $C_1$–$C_4$ alkyl and/or $C_1$–$C_4$ alkoxy, or is $C_1$–$C_{12}$ alkylene which is substituted by hydroxy, halogen and/or alkoxy, X is oxygen or sulfur, and $R_4$ is hydrogen, $C_1$–$C_{18}$ alkyl, phenyl or phenyl which is substituted by halogen, hydroxy, $C_1$–$C_4$ alkyl, $NO_2$ and/or $C_1$–$C_4$ alkoxy, or is $C_7$–$C_9$ phenylalkyl, and $R_3$ is hydrogen, $C_1$–$C_{20}$ alkyl, phenyl or phenyl which is substituted by halogen, hydroxy, $C_1$–$C_4$ alkyl, $NO_2$ and/or $C_1$–$C_4$ alkoxy, or is $C_7$–$C_9$ phenylalkyl. The process comprises carrying out a Claisen condensation of a ketone of formula III

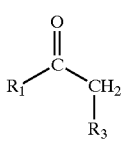
(III)

and an ester of formula IV

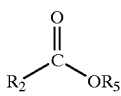
(IV)

or

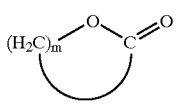
(V)

wherein m is 2 to 10 and $R_5$ is $C_1$–$C_5$ alkyl, phenyl or phenyl which is substituted by halogen, $C_1$–$C_4$ alkyl or hydroxy, the reaction being carried out with the base used as catalyst, a hydride of an alkali metal or alkaline earth metal or an alcoholate of $C_1$–$C_5$ alkali metal or $C_1$–$C_5$ alkaline earth metal, in a mixture of dimethyl sulfoxide and at least one organic solvent which is inert under the reaction conditions. The use of dimethyl sulfoxide is a disadvantage owing to the difficulty of completely removing it from the product and of recovering it for reuse without significant losses.

U.S. Pat. No. 5,672,646 discloses a stabilizing composition for a chlorine-containing polymer (PVC), characterized in that it comprises the unpurified crude product resulting from the reaction of an ester with a ketone in the presence of an alkaline agent, this crude product comprising at least 10% by weight of β-diketone and being in the form of a powder.

U.S. Pat. No. 5,808,165 discloses compositions containing beta-diketones of formula (I) and formula (II), $$R_1COCH_2COR_2 \quad (I)$$

$$R_2COCH_2COR_2 \quad (II)$$

which may be used to stabilize various polymers, such as polyvinyl chlorides (PVCs), in which $R_1$ is represented by the formula $$(Y)_n—\Phi—,$$

wherein Φ is phenyl and each Y, which may be the same or different, is a hydrogen atom or a group selected from hydrocarbon chains having 1 to 12 carbon atoms, alkoxys, silyls and nonreactive halogen atoms; each $R_2$, which may be the same or different, represents a hydrogen atom or a group selected from hydrocarbon chains having 1 or 5 to 12 carbon atoms, which may be interrupted by one or more oxygen atoms, aralkyls, alkoxys and silyls; and n represents an integer from 0 to 3; with the proviso that if the number of carbon atoms in $R_2$ in formula (1) is less than 5, the sum of the carbons contained in Y is at least 3 and at most 12, and that in formula (II) the total number of carbon atoms in the two $R_2$'s is at least 10.

Dibenzoylmethane (DBM) is currently produced commercially by means of a Claisen condensation of acetophenone and methyl benzoate in the solvent cumene with sodium methoxide being used as the base. This process, however, presents several problems:

1) the sodium methoxide is a very fine powder that is very reactive toward water and carbon dioxide from air and is extremely hard to handle;

2) sodium methoxide is insoluble in cumene, which complicates the production process; and 3) sodium methoxide is, after acetophenone, the second most expensive raw material for the manufacture of DBM.

Thus, an improved process for making 1,3-diketones is still needed by industry.

The disclosures of the foregoing are incorporated herein by reference in their entirety.

SUMMARY OF THE INVENTION

In accordance with this invention, there is provided a process of preparing a 1,3-diketone from a carboxylic acid ester and a ketone by a condensation reaction promoted by a basic condensing agent that overcomes the problems outlined above by using a novel basic condensing agent that is soluble in an aromatic hydrocarbon and is an alkali metal alkoxide of an alcohol having a boiling point of at least 100° C. at atmospheric pressure. By the use of this condensing agent according to the invention, the handling of reagents has been simplified, side reactions during condensation are minimized, and the yields of 1,3-diketone are increased significantly.

There is also provided, in accordance with this invention, a process for preparing the novel basic condensing agent by heating a mixture consisting essentially of an alcohol having a boiling point of at least 100° C. at atmospheric pressure, an alkali metal hydroxide, and an aromatic hydrocarbon, and removing water formed in the reaction of the alcohol with the alkali metal hydroxide.

There is, moreover, provided in accordance with this invention, a basic condensing agent consisting essentially of a solution of alkali metal alkoxide of an alcohol having a boiling point of at least 100° C. at atmospheric pressure in an aromatic hydrocarbon. The expression "consisting essentially of" is used to indicate that polar aprotic solvents such as dimethyl sulfoxide are unnecessary and objectionable according to this invention.

When the two processes according to the invention are combined, the alcohol used in preparing the basic condensing agent is regenerated in the preparation of the 1,3-diketone, and can be readily recovered and reused to prepare additional alkali metal alkoxide by reaction with alkali metal hydroxide according to the invention. Consequently, from an economic standpoint the only base consumed is alkali metal hydroxide, which offers significant savings over prior art sodium methoxide and other basic condensing agents.

More particularly, the present invention is directed to a method for the preparation of 1,3-diketones comprising the steps of:

(A) mixing an alkali metal base an aromatic hydrocarbon solvent and an alcohol having a boiling point of a least 100° C. at atmospheric pressure;

(B) boiling the mixture and distilling water formed by the reaction between the base and the alcohol, whereby a solution of a hindered alkali metal alkoxide is formed in the solvent (alternatively, alkali metal alkoxide can be dissolved or suspended in an aromatic hydrocarbon);

(C) mixing a carboxylic acid ester with the solution of the alkali metal alkoxide in the aromatic hydrocarbon solvent;

(D) adding a ketone to the mixture and heating at a temperature in the range of 40–150° C. until the formation of 1,3-diketone is substantially complete; and (E) recovering 1,3-diketone from the reaction mixture.

DESCRIPTION OF THE PREFERRED EMBODIMENT(s)

The process of the present invention is a Claisen condensation comprising the following steps:

1) The base for the condensation, a hindered sodium or potassium alkoxide, is preferably prepared in situ before the actual condensation takes place. This can be advantageously carried out by boiling a mixture of a hindered alcohol, sodium or potassium hydroxide (pellets or aqueous solution), and an aromatic hydrocarbon solvent. The water formed is distilled. A slow stream of nitrogen is maintained over the mixture.

2) The temperature of the mixture is adjusted to a predetermined value. The ester component, preferably a methyl ester, is added to the mixture. The ketone component is then added slowly and the mixture is stirred until no more product is formed.

3) The mixture is preferably acidified using an excess of acid, which is then neutralized, whereupon the solvent is stripped. Depending on its nature, the hindered alcohol can be recovered by distillation, crystallization, or extraction with solvents. The diketone product, if it is a solid, can be purified by crystallization.

Alternatively, the sodium or potassium salt of the diketone can, in some cases, be isolated by filtration before acidifying the reaction mixture. The solid diketone salt can then be neutralized by slowly adding it with stirring to a mixture of water and an aromatic hydrocarbon. At the same time, an acid, such as acetic acid, is added to keep the pH neutral at all times. The organic layer can then be washed and the solvent stripped.

The 1,3-diketones prepared in accordance with this invention are preferably linear 1,3-diketones of general formula I $$R_1-\overset{O}{\underset{}{C}}-\overset{H}{\underset{R_3}{C}}-\overset{O}{\underset{}{C}}-R_2 \quad \text{(I)}$$

wherein
$R_1$ and $R_2$ are independently selected from the group consisting of $C_1$–$C_{20}$ alkyl; phenyl; phenyl that is substituted by halogen, hydroxy, $NO_2$, $C_1$–$C_4$ alkyl and/or $C_1$–$C_4$ alkoxy; $C_7$–$C_9$ phenylalkyl; and radicals of formula II $$-A-X-R_4 \quad \text{(II)}$$

wherein
A is selected from the group consisting of $C_1$–$C_{12}$ alkylene; $C_1$–$C_{12}$ alkylene that is substituted by hydroxy, halogen and/or alkoxy; phenylene; and phenylene that is substituted with halogen, hydroxy, $NO_2$, $C_1$–$C_4$ alkyl and/or $C_1$–$C_4$ alkoxy;
X is oxygen or sulfur;
$R_4$ is selected from the group consisting of hydrogen; $C_1$–$C_{18}$, alkyl; phenyl; phenyl that is substituted with halogen, hydroxy, $C_1$–$C_4$ alkyl, $NO_2$ and/or $C_1$–$C_4$ alkoxy; and $C_7$–$C_9$ phenylalkyl; and
$R_3$ is selected from the group consisting of hydrogen; $C_1$–$C_{20}$ alkyl; phenyl; phenyl that is substituted with halogen, hydroxy, $C_1$–$C_4$ alkyl, $NO_2$, and/or $C_1$–$C_4$ alkoxy; and $C_7$–$C_9$ phenylalkyl;
wherein the process comprises a Claisen condensation of ketones of formula III $$R_1-\overset{O}{\underset{}{C}}-\overset{}{\underset{R_3}{CH_2}} \quad \text{(III)}$$

with esters of formula IV $$R_2-\overset{O}{\underset{}{C}}-OR_5 \quad \text{(IV)}$$

wherein $R_5$ is selected from the group consisting of $C_1$–$C_5$ alkyl; phenyl; and phenyl that is substituted with halogen, $C_1$–$C_4$ alkyl, or hydroxy;
or, if $R_2$ in formula I is —$(CH_2)_m$OH, also with cyclic esters of formula V $$(H_2C)_m\diagdown O\diagup C=O \quad \text{(V)}$$

wherein m is an integer of from 2 to 10.

In the above-described structural formulae, where $R_1$ and/or $R_2$ are $C_1$–$C_{20}$ alkyl, they may be linear or branched and are typically methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, and isomers and mixtures thereof. They are preferably $C_1$–$C_{18}$ alkyl, such as methyl, isopentyl, n-nonyl, pentadecyl or heptadecyl.

Where $R_1$ and/or $R_2$ are substituted phenyl, they preferably contain from 1 to 3, more preferably 1 or 2 substituents, most preferably one substituent.

Where $R_1$ and/or $R_2$ are ($C_1$–$C_4$ alkyl)phenyl, they are preferably phenyl substituted by 1 to 3, more preferably 1 or 2, alkyl groups, which are most preferably methyl groups. Typical examples include tolyl, xylyl, or mesityl.

Where $R_1$ and/or $R_2$ are halogen-substituted phenyl, they may be a phenyl ring that is substituted by one or more identical or different members selected from the group consisting of fluoro, chloro, and bromo, preferably chloro or bromo, and are typically chlorophenyl or dichlorophenyl.

Where $R_1$ and/or $R_2$ are $C_1$–$C_4$ alkoxy-substituted phenyl, they are typically methoxyphenyl, ethoxyphenyl, propoxyphenyl, butoxyphenyl, and isomers thereof.

Where $R_1$ and/or $R_2$ are $C_7$–$C_9$ phenylalkyl, they may be, for example, benzyl, phenylethyl, α-methylbenzyl, 3-phenylpropyl, or α,α-dimethylbenzyl. Benzyl is preferred.

$R_1$ and/or $R_2$ are preferably $C_1$–$C_{18}$ alkyl, phenyl, ($C_1$–$C_4$ alkyl)phenyl, or —A—X—$R_4$.

Where A is $C_1$–$C_{12}$ alkylene, it can be either linear or branched, but is preferably linear, alkylene. Typical examples of such radicals include methylene, ethylene, propylene, butylene, pentylene, hexylene, heptalene, octalene, nonalene, decylene, undecylene, dodecylene, and isomers thereof. Alkylenes of from 1 to 6 carbon atoms are preferred, and n-propylene or n-pentylene are most preferred.

Where A is unsubstituted or substituted phenylene, it is preferably o- or p-phenylene, more preferably, A is unsubstituted phenylene.

Where $R_4$ is $C_1$–$C_{18}$ alkyl, it may be linear or branched alkyl, as exemplified above in connection with $R_1$ and $R_2$ up to the corresponding number of carbon atoms.

Where $R_4$ is substituted phenyl or $C_7$–$C_9$ phenylalkyl, it can have the same meanings as given for $R_1$ and $R_2$.

$R_4$ is preferably hydrogen, $C_1$–$C_{18}$ alkyl, or phenyl.

Where $R_3$ is $C_1$–$C_{20}$ alkyl, substituted phenyl, or $C_7$–$C_9$ phenylalkyl, it can have the same meanings as given for $R_1$ and $R_2$.

$R_3$ is preferably hydrogen or $C_1$–$C_4$ alkyl, e.g., methyl, ethyl, propyl, butyl, or isomers thereof, but is more preferably hydrogen.

Where $R_5$ is $C_1$–$C_5$ alkyl, it can be methyl, ethyl, propyl, butyl, butyl, pentyl, or isomers thereof. More preferably, $R_5$ is $C_1$–$C_4$ alkyl, most preferably, methyl.

Where $R_5$ is ($C_1$–$C_4$ alkyl)phenyl, it can have the same meanings as those given for $R_1$ and $R_2$.

As stated above, the basic condensing agent according to the invention is an alkali metal alkoxide of an alcohol, said alcohol having a boiling point of at least 100° C. at atmospheric pressure. The alkali metal of the alkoxide is any one or more of the alkali metals. Sodium and potassium alkoxides are preferred. The alcohol with a boiling point of at least 100° C. at atmospheric pressure can be primary, secondary, or tertiary, and can have 1–2 alcoholic hydroxyl groups. The alcohol can be aliphatic or cycloaliphatic, and can also be substituted with alkoxy groups having 1 to 5 carbon atoms and with aryl groups. Alkoxides of alcohols having a sterically hindered structure are particularly preferred. Preferred alkoxides are the sodium and potassium alkoxides of 1-butanol, 1-pentanol, cyclohexanol, 2-methyl-2,4-pentanediol, 2- propoxy-1- ethanol, 1-methoxy-2-propanol, 1-t-butoxy-2-propanol, 2-ethyl-1-hexanol, 1-phenylethanol, benzhydrol, triphenylmethanol, tert.-pentanol, 1-octanol, and 2-octanol, and the like.

The alkali metal alkoxide condensing agent can be prepared by reaction of the selected alcohol in the presence of aromatic hydrocarbon with such source of metal base as alkali metal or alkali metal hydride, with displacement of hydrogen; alkali metal amide, with displacement of ammonia; and lower alkali metal alkoxide, with displacement of lower alcohol. The alkali metal alkoxide condensing agent can also be prepared by dissolving a separately prepared alkali metal alkoxide of the selected alcohol in an aromatic hydrocarbon. In a particularly preferred emobidment, the alkali metal alkoxide is prepared according to the invention by reaction of the selected alcohol with alkali metal hydroxide, preferably sodium or potassium hydroxide, as the alkali metal base, with displacement of water. This can be advantageously carried out by heating a mixture of the selected alcohol, alkali metal hydroxide, and aromatic hydrocarbon solvent such that the water formed is distilled azeotropically, while maintaining a slow stream of nitrogen over the reaction mixture.

As disclosed above, ketones of formula III

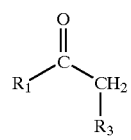
(III)

are employed as starting materials in the process of the present invention. Ketones that can be employed include aliphatic-aromatic, aliphatic-aliphatic, and cycloaliphatic ketones, such as acetophenone, acetone, methyl ethyl ketone, methyl n-propyl ketone, diethyl ketone, hexanone-2, pinacolone, di-n-propyl ketone, diisopropyl ketone, di-n-amyl ketone, chloroacetone, s-dichloroacetone, cyclohexanone, cyclopentanone, and the like.

As also disclosed above, another of the starting materials employed in the practice of the present invention are esters of formula IV

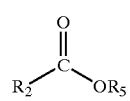
(IV)

wherein $R_5$ is selected from the group consisting of $C_1$–$C_5$ alkyl; phenyl; and phenyl that is substituted with halogen, $C_1$–$C_4$ alkyl, or hydroxy; or, if $R_2$ in formula I is —$(CH_2)_m$OH, also with cyclic esters of formula V

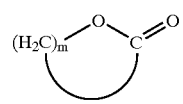
(V)

wherein m is an integer of from 2 to 10. Such esters include, for example, aromatic esters, such as methyl benzoate, and aliphatic esters, such as ethyl acetate, methyl esters of linear $C_8$ to $C_{18}$ carboxylic acids, such as methyl stearate, methyl palmitate, methyl caprylate, mixtures of aliphatic esters, and the like.

Alcohols, e.g., methanol, can, if desired, be removed from the reaction mixture by distillation during the condensation, although it was observed in several cases that this might lead to transesterification and a decrease in overall yield.

In one preferred aspect of the present invention, aromatic beta-diketones can be prepared.

Exemplary of such aromatic beta-diketones are dibenzoylmethane, benzoyl 2,4-methylenedioxy benzoylmethane; benzoyl 3,5-dimethylbenzoyl methane; benzoyl 3-methylbenzoylmethane; benzoyl 4-methyl benzoylmethane; 3-methylbenzoyl 4-methylbenzoylmethane; benzoyl 4-chlorobenzoylmethane; benzoyl 2-bromobenzoylmethane; benzoyl 3,5-dichlorobenzoylmethane; benzoyl 2-nitrobenzoylmethane; benzoyl-2,3,4-trimethylbenzoylmethane; benzoyl-2,3,5-trichlorobenzoylmethane; benzoylstearoylmethane; 3-methylbenzoylstearoylmethane 3,4-dichlorobenzoylstearoylmethane benzoyl heptadecanoylmethane; 3-methylbenzoyltetradecanoylmethane; 4-chlorononadecoylmethane; 2-methylbenzoylauroylmethane; 3-nitrobenzoylmyristoylmethane; 2,3-ethoxybenzoyl palmitoylmethane; 2-methoxy benzoylstearoylmethane, 3-methylthio benzoyl 2,3-butylmethane and the like.

In order to prepare these and other beta-diketones, a corresponding acetophenone-type reactant is preferably selected. Exemplary of such useful acetophenone reactants are acetophenone; o-, m-, or p-methylacetophenone; o-, m-, or p-methoxy acetophenone; o-, m-, or p-methylthioacetophenone, o-, m-, or p-nitroacetophenone; 3,4-(methylenedioxy) acetophenone, o-, m-, or p-chloroacetophenone; o-, m-, or p-bromoacetophenone; 2,4-diethylacetophenone; 2,3,5-trichloroacetophenone, 2,3-dibromoacetophenone; 2,4-dimethoxyacetophenone; 2,4-propoxyacetophenone; 2,3-dimethylthioacetophenone; and the like.

Similarly, the ester reactant is selected on the basis of the identity of the desired betaketone. For example, an ester of benzoic acid can be used. Since the condensation reaction has as its by-product an alcohol formed from the ester group, normally there is no benefit from using higher alkyl esters. Accordingly, lower alkyl esters of benzoic acid are satisfactory, although higher esters can be used, if desired. In this description of the invention, the term "lower" means alkyl groups having up to about 5 carbon atoms.

Exemplary of such benzoate reactants are methylbenzoate; ethyl benzoate; propylbenzoate; butylbenzoate; pentylbenzoate; methyl o-,m- or p-methylbenzoate; ethyl o-, m-, or p-chlorobenzoate; methyl o-, m-, or p-methylthiobenzoate; ethyl o-, m-, or p-methoxybenzoate; methyl o-, m-, or p- bromobenzoate; ethyl o-, m-, or p-nitrobenzoic acid; ethyl 2,3-dimethyl benzoate; propyl 2,5-diethylbenzoate; ethyl 2,3,4-tri-methylbenzoate; butyl2,5-diethylthiobenzoate; ethyl 3,4-dimethoxybenzoate; methyl 2,3-dichlorobenzoate; ethyl 2,4-dibromobenzoate; propyl 2,3,5-trichlorobenzoate; propyl 2,4-diethyoxybenzoate and the like.

The condensation reaction can be performed at various elevated temperatures. In order to optimize the yield and purity of a beta-diketone product, temperatures between about 40° C. and about 170° C., preferably about 90° C. to about 120° C., are normally used. At these temperatures maximum amounts of high quality beta-diketone products can be recovered by standard procedures.

In order to obtain high quality product in high yield, it is desirable to use a molar excess of the ester reactant. This causes the reaction to proceed to about its theoretical maximum. The preferred excess of ester reactant useful in this process varies somewhat with the identity of the ester reactant. Since the use of more than the necessary amount of ester reactant will often increase the loss of this reactant, it is preferred to maintain the ratio of ester reactant to acetophenone below about 8:1, more preferably below about 2:1. Ratios of the ester of benzoic acid to acetophenone of about 2:1 will normally produce optimum yields and purity of dibenzoylmethane. The excess ester reactant can be recycled with the solvent so as to limit the reactant needs and reduce the cost of operating the process.

Aromatic hydrocarbons are preferably used as solvents for performing the process of the present invention. Since the temperature of the reaction is between about 100° C. and about 170° C., it is desirable to use an aromatic hydrocarbon solvent having a boiling point within this temperature range so that the reaction can proceed at atmospheric pressure; however, aromatic hydrocarbons having lower or higher boiling points can be used by adjusting the pressure accordingly. Among the aromatic hydrocarbons useful as solvents in the practice of the process of the present invention are ethyl benzene, cymene, diethylbenzene, dimethylethylbenzene, amyltoluene, toluene, trimethylbenzene, cumene, tetralin, xylenes, and the like.

At the end of the reaction, the 1,3-diketone is present in the reaction mixture in the form of an alkali metal salt. In some cases the salt can be isolated from the reaction mixture by filtration and used as is or converted to other 1,3-diketone metal salts, for example aluminum, calcium, magnesium, and zinc salts, by reaction with a compound of the selected metal such as aluminum sulfate, calcium and magnesium chlorides, and zinc acetate.

The solid dikidetone salt can also be neutralized to afford the free 1,3-diketone by slowly adding it with stirring to a mixture of water and an aromatic hydrocarbon while adding an acid, such as acetic acid, to keep the pH neutral. The organic layer can then be washed and the solvent stripped.

Alternatively, the entire reaction mixture can be acidified with an excess of acid, which is then neutralized, and the solvent is stripped. The alcohol reactant can be recovered together with the solvent or separately, by such techniques as distillation, crystallization or extraction with solvents as appropriate. The diketone product, if it is a solid, can be purified by crystallization.

Various features and aspects of the present invention are illustrated further in the examples that follow. While these examples are presented to show one skilled in the art how to operate within the scope of the invention, they are not intended in any way to serve as a limitation upon the scope of the invention.

EXAMPLES

Example 1

Preparation of Dibenzoylmethane (DBM)

1-Methoxy-2-propanol (923 g; 10.24 mol), sodium hydroxide (256 g; 6.4 mol), and xylenes (1820 g; 2.12 L) were placed into a four-necked, round bottom, five liter flask equipped with a stirrer, a thermometer, and an Oldershaw column with a Dean-Stark trap and a condenser. The mixture was heated to boiling with stirring under a blanket of nitrogen and the water was azeotroped out (temperature of reflux 106–116° C.). When no more water was collected (280 mL of lower phase), some solvent was distilled off (1,200 mL), while xylenes (432.2 g, dry) were replaced, until no more alcohol was detected in the distillate. The mixture in the flask was cooled down to and kept at 95° C., and the fractionation column and trap were replaced with a reflux condenser, while maintaining the nitrogen stream.

Methyl benzoate (1089 g; 8.0 mol) was added and slow addition (over a period of 38 minutes) of acetophenone (481 g; 4.0 mol) by means of a peristaltic pump was begun. After 75 minutes from the beginning of the addition of the ketone, the mixture was cooled down (an ice bath was used), and then acidified by the slow addition of 98% sulfuric acid (392 g) with stirring. Sodium bicarbonate (185 g) was added for neutralizing the mixture. The slurry was distilled under vacuum (18 cm Hg, $T_{pot}$=84° C.), and at the same time 1,400 g of xylenes was added. The distillate (2,094 g) contains methoxypropanol, which can be recovered (see below).

The residue was transferred to a separatory funnel and washed with water. The solvents were stripped in a Rotavap at 2 mm Hg, heating up to 145° C. The distillate contains methyl benzoate for recovery.

The crude DBM solidified upon cooling and was crystallized from 80% isopropanol, affording DBM (684.5 g, 76.3% yield) having a purity of 99% (GC). 1-Methoxy-2-propanol was recovered by distillation of both the lower phase of the distillate from the azeotropic distillation and the solvent/alcohol distillation, as well as from the reduced pressure distillation of the slurry. As much as 80% of the alcohol was recovered. Methyl benzoate (353.9 g) was also recovered (by reduced pressure distillation), as well as 96% of the xylenes utilized.

Example 2

Preparation of Dibenzoylmethane (DBM)

Benzhydrol (189.77 g; 1.03 mol), potassium hydroxide (84.3%; 66.56 g; 1.0 mol) and cumene (375 mL) were placed into a four-necked, round bottom, one liter flask equipped with a stirrer, a thermometer, and an Oldershaw column with a Dean-Stark trap and a condenser. The mixture was heated to boiling with stirring under a blanket of nitrogen and the water was azeotroped out (temperature of reflux 148–150° C). When no more water was collected (27 mL, yield=95%, about 2 hours) the mixture was cooled down to and kept at 90° C. The fractionation column and trap were replaced with a reflux condenser, while maintaining the nitrogen stream. Methyl benzoate (181.5 g; 1.33 mol) was added at once, and slow addition (12 minutes) of acetophenone (80.10 g; 0.667 mol) by means of a syringe pump was begun. After 60 minutes from the beginning of the addition of the ketone, the mixture was allowed to cool to room temperature, whereupon it was acidified with 10% sulfuric acid. The cumene layer was washed with a saturated solution of sodium bicarbonate in water and then with water. The organic layer was then concentrated under vacuum in a rotary evaporator. The residue was crystallized from 90% isopropanol, affording DBM (112.13 g, 75% yield) having a purity of 98% (GC).

Benzhydrol was recovered from the mother liquor using the same procedure used in Example 4 infra.

Example 3

Preparation of Dibenzoylmethane (DBM)

Cumene (dry, 350 mL), sodium tert-pentoxide (35.8 g; 0.325 mol), and methyl benzoate (68.1 g; 0.50 mol) were placed into a four-necked, round bottom, one liter flask equipped with a stirrer, a thermometer, and a reflux condenser with a distillation valve. The mixture was heated to 120° C. and kept at that temperature under a blanket of nitrogen.

Acetophenone (30.0 g; 0.25 mol) was added slowly over a period of 36 minutes by means of a syringe pump. Some solvent (37 mL total) was distilled out of the system as the reaction proceeded. A vacuum was applied to the system by means of a water aspirator to help with the distillation. After 1.4 hours from the beginning of the addition of the ketone, the mixture was cooled down to room temperature and filtered under vacuum. The sodium salt of DBM was washed with dry cumene.

Into a two liter beaker equipped with a mechanical stirrer, 500 mL of water and 250 mL of cumene were added. A ph-stat (Metrohm titrator, model 716 DMS, Brinkmann Instruments) was set up to add acetic acid to pH 7. The sodium salt of DBM was added slowly to the beaker. The pH varied between 5 and 7.5; 14.7 mL of acetic acid was added. The two layers were transferred to a separation funnel, the aqueous layer was removed, and the organic layer was washed with aqueous sodium bicarbonate and then with water. The organic layer was then concentrated under vacuum in a rotary evaporator. The residue was crystallized from 90% isopropanol, affording DBM (53.58 g, 96% yield) having a purity of more than 99% (GC).

Example 4

Preparation of Benzoylstearoylmethane (SBM)

Benzhydrol (104.3 g; 0.567 mol), potassium hydroxide (85.4%; 36.14 g; 0.550 mol) and cumene (375 mL) were placed into a four-necked, round bottom, one liter flask equipped with a stirrer, a thermometer, and an Oldershaw column with a Dean-Stark trap and a condenser. The mixture was heated to boiling with stirring under a blanket of nitrogen and the water was azeotroped out (temperature of reflux 148–150° C.). When no more water was collected (14.4 mL, yield=93 %, about 2 hours) the mixture was cooled down to and kept at 100° C. The fractionation column and trap were replaced with a reflux condenser, while maintaining the nitrogen stream. Methyl stearate (126.97 g; 0.425 mol; preheated to 100° C.) was added at once, and slow addition (12 minutes) of acetophenone (44.06 g; 0.367 mol) by means of a syringe pump was begun. After 70 minutes from the beginning of the addition of the ketone, the mixture was allowed to cool to room temperature, and was acidified with 10% sulfuric acid. The cumene layer was washed with water until the washes were neutral, and then concentrated under vacuum in a rotary evaporator. The residue was crystallized from methanol, affording SBM (105.0 g, 74% yield) having a purity of 98% (GC).

The mother liquor from the crystallization was concentrated and the residue was crystallized from heptane, yielding 68.83 g of pure benzhydrol (66% recovered). More benzhydrol (14.6 g; 14% yield), as well as methyl stearate (15.05 g–12.3% yield), were recovered by evaporating the heptane and fractionally distilling the residue under vacuum (130–205° C. at 7 mm Hg).

Example 5

Preparation of Benzoylstearoylmethane (SBM)

A procedure analogous to the one described in Example 4 was used for obtaining a mixture of 1,3-diketones, with benzoylstearoylmethane as the main component. The methyl ester used as raw material was Kemester 7018 (Crompton), with a chain length distribution of $C_{14}$: 4.4 weight percent; $C_{16}$: 27.9%; $C_{17}$: 2.6%; and $C_{18}$: 61.4%. The amount used was 122.4 g; 0.425 mol. Crystallization from methanol afforded 83.4 g of SBM (61% yield) of purity higher than 99% (GC).

In order to recover benzhydrol, the mother liquor from the methanol crystallization was concentrated and steam distilled. Upon cooling, the distillate was filtered and the benzhydrol was washed with a small amount of heptane. A liquid organic phase in the filtrate was vacuum distilled (130–205° C. at 7 mm Hg), affording additional benzhydrol and Kemester 7018. Total benzhydrol and Kemester 7018 recovered was 79.3 g (76% yield) and 12.24 (10% yield), respectively.

Example 6

Preparation of Benzoylstearoylmethane (SBM)

Xylenes (dry, 180 mL), sodium tert-pentoxide (17.9 g; 0.163 mol), and methyl stearate (41.5 g; 0.139 mol) were placed into a four-necked, round bottom, half-liter flask equipped with a stirrer, a thermometer, and a reflux condenser with a distillation valve. The mixture was heated to 120° C. and kept at that temperature under a blanket of nitrogen. Acetophenone (15.0 g; 0.125 mol) was added slowly over a period of 30 minutes by means of a syringe pump. After 42 minutes, the distillation valve was opened and the distillate was removed as the reaction proceeded. After 1:05 hours from the beginning of the addition of the ketone, the mixture was cooled down to room temperature. Aqueous sulfuric acid (16%) was added with stirring until the pH of the aqueous layer was acidic.

The organic layer was washed in a separation funnel with aqueous sodium bicarbonate and then with water. The solvents were evaporated on a Rotovap, and the solid residue was crystallized from methanol, affording SBM (35.7 g, 74% yield) having a purity of 98% (GC).

Example 7

Preparation of Benzoylstearoylmethane (SBM)

In a procedure analogous to Example 6, acetophenone was condensed with methyl stearate in cumene using sodium tert-butoxide (15.6 g, 0.163 mol). The acetophenone (15.0 g; 0.125 mol) was added over a period of 28 min, and no methanol was removed from the mixture by distillation. Crude SBM (44.76 g) was obtained. This crude was not purified by crystallization. It was possible, however, to quantitate the amount of SBM present by running a proton NMR spectrum at 54° C. of a sample dissolved in deuterated methanol. The total amount of SBM in the product was 32.65 g, that is, 73% of the sample, corresponding to a yield of 67% for the condensation. The impurities mainly comprised stearic acid and unreacted methyl stearate.

Example 8

Preparation of Benzoylcapryloylmethane (CBM)

A procedure analogous to that described in Example 5 was used for obtaining a liquid mixture of 1,3-diketones, using CE-810 (Procter & Gamble) as the starting methyl ester. This ester had the following chain length distribution: $C_6$: 4.1 weight %; $C_8$: 52.8%; $C_{10}$: 42.7%; and $C_{12}$: 0.3%. For the preparation of potassium benzhydroxide, 103.36 g (0.561 mol) of benzhydrol was reacted with 0.55 mol of potassium hydroxide as described in Example 4. After addition of the ester (71.5 g; 0.425 mol), acetophenone (44.06 g; 0.367 mol) was added over a period of 12 minutes and the mixture was allowed to react for a total of 70 minutes. The mixture was allowed to cool to room temperature, and was acidified with 10% sulfuric acid. The cumene layer was washed with water until the washes were neutral, and then concentrated under vacuum in a rotary evaporator. The residue was treated with heptane, allowed to stand for a few minutes, and then filtered, affording pure benzhydrol (63.2 g; 61.1% yield). The heptane was removed under vacuum. More benzhydrol was obtained by adding 500 mL of heptane, 500 mL of methanol, and 250 mL of water, stirring, removing the lower layer, and repeating this extraction several times. Upon evaporation of the lower layer under vacuum in a rotary evaporator, and washing the resulting crystals with heptane, 17.3 g of benzhydrol (16.7% yield) was obtained. Evaporation of the solvents in the upper layer afforded 80.0 g (85% yield) of CBM with a purity of over 95% (GC).

Example 9

Preparation of Acetylacetone (AcAc)

1-Methoxy-2-propanol (184.6 g; 2.048 mol), sodium hydroxide (51.2 g; 1.28 mol), and xylenes (424 mL) were placed into a four-necked, round bottom, one liter flask equipped with a stirrer, a thermometer, and an Oldershaw column with a Dean-Stark trap and a condenser. The mixture was heated to boiling with stirring under a blanket of nitrogen and the water was azeotroped out (temperature of reflux 108–121° C.). When no more water was collected (67 mL of lower phase), some solvent was distilled off (240 mL) while xylenes (100 g, dry) were replaced, until no more alcohol was detected in the distillate. The mixture in the flask was cooled down to and kept at 55° C., and the fractionation column and trap were replaced with a reflux condenser, while maintaining the nitrogen stream. Ethyl acetate (120.84 g; 1.37 mol) was added at once and slow addition of acetone (53.10 g; 0.91 mol) over a period of 10.5 minutes was begun. After 80 minutes from the beginning of the addition of the ketone, the mixture was cooled down to room temperature and acidified by slow addition of 98% sulfuric acid (87.63 g) with stirring. Solid sodium bicarbonate (48.6 g) was added and the mixture was warmed to 45° C. in order to neutralize it. The slurry was filtered and washed with a small amount of xylenes. Volatile solvents, such as acetone, methanol, 1-methoxy-2-propanol, and ethyl acetate, were removed from the filtrate by fractional distillation. GC analysis of the resulting AcAc solution in xylenes showed that there were 62.9 g of AcAc. This was confirmed by titration of a sample dissolved in 50/50 toluene/methanol with 1 M sodium hydroxide (Metrohm titrator, model 716 DMS, Brinkmann Instruments) (pK 11.76). This corresponds to a 60% yield based on acetone.

Example 10

Preparation of 2-Benzoylcyclohexanone (BCH)

Cumene (dry, 180 mL), sodium tert-pentoxide (35.8 g; 0.326 mol), and methyl benzoate (68.1 g; 0.50 mol) were placed into a four-necked, round bottom, half-liter flask equipped with a stirrer, a thermometer, and a reflux condenser. The mixture was heated to 100° C. and kept at that temperature under a blanket of nitrogen. Cyclohexanone (24.5 g; 0.250 mol) was added slowly over a period of 15 minutes by means of a syringe pump. After 20 minutes from the beginning of the addition of the ketone, the mixture was cooled with an ice water bath to room temperature. Aqueous sulfuric acid (10%) was added with stirring, keeping the temperature below 25° C., until the pH of the aqueous layer was acidic. The organic layer was washed in a one liter separation funnel with aqueous sodium bicarbonate and then with water. The solvents were evaporated on a Rotovap and the residue was crystallized from heptane, affording BCH (38.43 g, 76% yield) having a purity of 99% (GC).

Example 11

Preparation of 2-Benzoylcyclohexanone (BCH)

1-Methoxy-2-propanol (61.3 g; 0.68 mol), sodium hydroxide (16.0 g; 0.40 mol), and xylenes (300 mL) were placed into a four-necked, round bottom, half-liter flask equipped with a stirrer, a thermometer, and an Oldershaw column with a Dean-Stark trap and a condenser. The mixture was heated to boiling with stirring under a blanket of nitrogen and the water was azeotroped out (temperature of reflux 106–116° C.). When no more water was collected (23 mL of lower phase) some solvent was distilled off (215 mL), while xylenes (432.2 g, dry) were replaced, until no more alcohol was detected in the distillate (temperature of reflux 137° C.). The mixture in the flask was cooled down to and kept at 80° C. and the fractionation column and trap were replaced with a reflux condenser while maintaining the nitrogen stream. Methyl benzoate (68.1 g; 0.50 mol) was added, and slow addition over a period of 10 minutes of cyclohexanone (24.5 g, 0.250 mol) by means of a syringe pump was begun. After 19 minutes from the beginning of the addition of the ketone, the mixture was cooled down (an ice bath was used), and acidified by slow addition of 98% sulfuric acid (slightly over 24.5 g) with stirring. The mixture was transferred to a 1 L separatory funnel, washed with aqueous sodium bicarbonate, and then with water. Evaporation of the organic layer under vacuum and recrystallization from heptane afforded 32.86 g of BCH (65% yield based on cyclohexanone), with a purity of 99% (GC).

In view of the many changes and modifications that can be made without departing from principles underlying the invention, reference should be made to the appended claims for an understanding of the scope of the protection afforded the invention.

What is claimed is:

1. A method for the preparation of 1,3-diketones comprising the steps of:
   (A) providing a mixture of an alkali metal hydroxide, an aromatic hydrocarbon, and an alcohol having a boiling point of a least 100° C. at atmospheric pressure;
   (B) heating the mixture and removing non-alkoxide by-product formed by reaction of the alkali metal hydroxide and the alcohol, whereby a solution of an alkali metal alkoxide in the aromatic hydrocarbon is formed;
   (C) mixing a carboxylic acid ester with the solution of the alkali metal alkoxide;
   (D) adding a ketone and heating at a temperature in the range of 40–150° C. until the formation of 1,3-diketone is substantially complete; and
   (E) recovering 1,3-diketone from the reaction mixture.

2. The method of claim 1, wherein the 1,3-diketone is recovered in the form of an alkali metal salt thereof.

3. The method of claim 1, wherein the 1,3-diketone is recovered as the free diketone.

4. The method of claim 3, wherein the reaction mixture is acidified, excess acid is neutralized, an aqueous layer is separated from an organic layer, and the 1,3-diketone is recovered from the organic layer.

5. The method of claim 1 wherein the alkali metal hydroxide is sodium hydroxide or potassium hydroxide.

6. The method of claim 1 wherein the alcohol is selected from the group consisting of 1-butanol, 1-pentanol, cyclohexanol, 2-methyl-2,4-pentanediol, 2-propoxy-1-ethanol, 1-methoxy-2-propanol, 1-t-butoxy-2-propanol, 2-ethyl-1-hexanol, 1-phenylethanol, benzhydrol, triphenylmethanol, tert.-pentanol, 1-octanol, and 2-octanol.

7. The method of claim 1 wherein the aromatic hydrocarbon solvent is selected from the group consisting of ethyl benzene, cymene, diethylbenzene, dimethylethylbenzene, amyltoluene, toluene, trimethylbenzene, cumene, tetralin, and xylenes.

8. The method of claim 1 wherein the diketone is of the structure

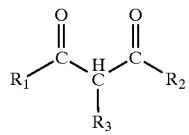

wherein $R_1$ and $R_2$ are independently selected from the group consisting of $C_1$–$C_{20}$ alkyl; phenyl; phenyl that is substituted by halogen, hydroxy, $NO_2$, $C_1$–$C_4$ alkyl and/or $C_1$–$C_4$ alkoxy; $C_7$–$C_9$ phenylalkyl; and radicals of formula II

wherein

A is selected from the group consisting of $C_1$–$C_{12}$ alkylene; $C_1$–$C_{12}$ alkylene that is substituted by hydroxy, halogen and/or alkoxy; phenylene; and phenylene that is substituted with halogen, hydroxy, $NO_2$, $C_1$–$C_4$ alkyl and/or $C_1$–$C_4$ alkoxy;

X is oxygen or sulfur;

$R_4$ is selected from the group consisting of hydrogen; $C_1$–$C_{18}$ alkyl; phenyl; phenyl that is substituted with halogen, hydroxy, $C_1$–$C_4$ alkyl, $NO_2$ and/or $C_1$–$C_4$ alkoxy; and $C_7$–$C_9$ phenylalkyl; and $R_3$ is selected from the group consisting of hydrogen; $C_1$–$C_{20}$ alkyl; phenyl; phenyl that is substituted with halogen, hydroxy, $C_1$–$C_4$ alkyl, $NO_2$, and/or $C_1$–$C_4$ alkoxy; and $C_7$–$C_9$ phenylalkyl.

9. The method of claim 8 wherein the ketone is of the structure

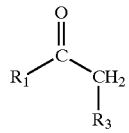

10. The method of claim 1 wherein the ketone is selected from the group consisting of acetophenone; o-, m-, or p-methylacetophenone; o-, m-, or p-methoxy acetophenone; o-, m-, or p-methylthioacetophenone, o-, m-, or p-nitroacetophenone; 3,4-(methylenedioxy) acetophenone, o-, m-, or p-chloroacetophenone; o-, m-, or p-bromoacetophenone; 2,4-diethylacetophenone; 2,3,5-trichloroacetophenone, 2,3-dibromoacetophenone; 2,4-dimethoxyacetophenone; 2,4-propoxyacetophenone; and 2,3-dimethylthioacetophenone.

11. The method of claim 8 wherein the ester is of the structure

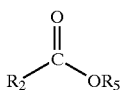

wherein $R_5$ is selected from the group consisting of $C_1$–$C_5$ alkyl; phenyl; and phenyl that is substituted with halogen, $C_1$–$C_4$ alkyl, or hydroxy.

12. The method of claim 11 wherein the ester is a benzoate.

13. The method of claim 12 wherein the benzoate is selected from the group consisting of methylbenzoate; ethyl benzoate; propylbenzoate; butylbenzoate; pentylbenzoate; methyl o-, m-or p-methylbenzoate; ethyl o-, m-, or p-chlorobenzoate; methyl o- m-, or p-methylthiobenzoate; ethyl o-, m-, or p-methoxybenzoate; methyl o-, m-, or p-bromobenzoate; ethyl o-, m-, or p-nitrobenzoic acid; ethyl 2,3-dimethyl benzoate; propyl 2,5-diethylbenzoate; ethyl 2,3,4-tri-methylbenzoate; butyl-2,5-diethylthiobenzoate; ethyl 3,4-dimethoxybenzoate; methyl 2,3-dichlorobenzoate; ethyl 2,4-dibromobenzoate; propyl 2,3,5-trichlorobenzoate; and propyl 2,4-diethyoxybenzoate.

14. The method of claim 1 wherein the diketone is an aromatic beta-diketone.

15. The method of claim 14 wherein the aromatic beta-diketone is selected from the group consisting of dibenzoylmethane, benzoyl 2,4-methylenedioxy benzoylmethane; benzoyl 3,5-dimethylbenzoyl methane; benzoyl 3-methylbenzoylmethane; benzoyl 4-methyl benzoylmethane; 3-methylbenzoyl 4-methylbenzoylmethane; benzoyl 4-chlorobenzoylmethane; benzoyl 2-bromobenzoylmethane; benzoyl 3,5-dichlorobenzoylmethane; benzoyl 2-nitrobenzoylmethane; benzoyl-2,3,4-trimethylbenzoylmethane; benzoyl-2,3,5-trichlorobenzoylmethane; benzoylstearoylmethane; 3-methylbenzoylstearoylmethane 3,4-dichlorobenzoylstearoylmethane benzoyl heptadecanoylmethane; 3-methylbenzoyltetradecanoylmethane; 4-chloro-nonadecoylmethane; 2-methylbenzoylauroylmethane; 3-nitrobenzoylmyristoylmethane; 2,3-ethoxybenzoyl palmitoylmethane; 2-methoxy benzoylstearoylmethane, and 3-methylthio benzoyl 2,3-butylmethane.

16. The method of claim 8 wherein $R_2$ is —$(CH_2)_m$ OH and the ester is of the structure

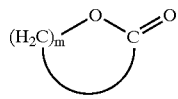

wherein m is an integer of from 2 to 10.

17. A method for the preparation of 1,3-diketones comprising the steps of:

(A) adding an alkali metal hydroxide and a hindered alcohol to an aromatic hydrocarbon solvent;

(B) boiling the mixture formed in step (A) and azeotropically distilling water formed by the reaction between the alkali metal hydroxide and the alcohol, whereby a solution of a hindered alkali metal alkoxide is formed in situ in the aromatic hydrocarbon solvent;

(C) mixing an ester with the solution of the hindered alkali metal alkoxide in the aromatic hydrocarbon solvent; and then (D) adding a ketone to the mixture.

18. The method of claim 17 further comprising the steps of (E) acidifying the mixture; and (F) neutralizing any excess acid.

19. The method of claim 17 further comprising the step of isolating the diketone product.

20. The method of claim 18 further comprising the step of isolating the diketone product.

* * * * *